United States Patent
Ross et al.

[11] Patent Number: 5,935,961
[45] Date of Patent: Aug. 10, 1999

[54] PYRIDAZINONES AND THEIR USE AS FUNGICIDES

[75] Inventors: Ronald Ross, Jamison; Steven Howard Shaber, Horsham, both of Pa.

[73] Assignee: Rohm and Haas Company, Phila., Pa.

[21] Appl. No.: 09/050,308

[22] Filed: Mar. 30, 1998

Related U.S. Application Data

[62] Division of application No. 08/660,244, Jun. 7, 1996, Pat. No. 5,763,440, which is a continuation of application No. 08/337,712, Nov. 14, 1994, abandoned.

[51] Int. Cl.⁶ .................................................. A01W 43/58
[52] U.S. Cl. ........................................... 514/253; 544/238
[58] Field of Search ............................ 544/238; 514/253

[56] References Cited

U.S. PATENT DOCUMENTS

| | | | |
|---|---|---|---|
| 4,826,531 | 5/1989 | Anthony et al. | 544/238 |
| 4,937,372 | 6/1990 | Wenderoth et al. | 560/55 |
| 4,999,042 | 3/1991 | Anthony et al. | 514/276 |
| 5,034,388 | 7/1991 | Clough et al. | 544/239 |
| 5,041,618 | 8/1991 | Brand et al. | 560/104 |
| 5,088,526 | 2/1992 | Nash et al. | 141/1 |
| 5,145,980 | 9/1992 | Wenderoth et al. | 560/35 |
| 5,157,037 | 10/1992 | Schuetz et al. | 514/269 |
| 5,157,144 | 10/1992 | Anthony et al. | 560/35 |
| 5,158,954 | 10/1992 | Clough et al. | 544/238 |
| 5,185,342 | 2/1993 | Hayase et al. | 514/274 |
| 5,194,438 | 3/1993 | Schuetz et al. | 514/269 |
| 5,221,691 | 6/1993 | Clough et al. | 514/617 |
| 5,240,925 | 8/1993 | Shaber et al. | 514/336 |
| 5,252,594 | 10/1993 | Shaber et al. | 514/383 |
| 5,315,025 | 5/1994 | Bushell et al. | 560/60 |
| 5,342,837 | 8/1994 | Clough | 514/247 |
| 5,346,902 | 9/1994 | Clough et al. | 544/239 |
| 5,401,763 | 3/1995 | Camaggi et al. | 544/239 |
| 5,453,427 | 9/1995 | Eberle et al. | 544/238 |
| 5,506,254 | 4/1996 | Kirstgen et al. | 544/238 |
| 5,552,409 | 9/1996 | Michelotti et al. | 544/239 |
| 5,631,254 | 5/1997 | Michelotti et al. | 544/239 |
| 5,635,494 | 6/1997 | Ross et al. | 544/239 |

FOREIGN PATENT DOCUMENTS

| | | | |
|---|---|---|---|
| 72238 | 8/1984 | European Pat. Off. . | |
| 178826 | 4/1986 | European Pat. Off. . | |
| 283271 | 10/1988 | European Pat. Off. . | |
| 0 478 175 | 4/1992 | European Pat. Off. | 544/239 |
| 0478875 | 4/1992 | European Pat. Off. | 544/239 |
| 478875 | 4/1992 | European Pat. Off. . | |
| 9419331 | 9/1991 | Germany . | |
| 1533010 | 9/1976 | United Kingdom . | |

OTHER PUBLICATIONS

Shaber et al, Chem. Abstr. vol. 125, entry86658 abstracting EP 711759, 1996.

*Primary Examiner*—Donald G. Daus
*Attorney, Agent, or Firm*—Guy T. Donatiello

[57] ABSTRACT

Compounds with fungicidal properties having formula I

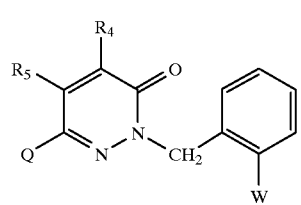

wherein
W is $CH_3-O-A=C(-)-CO(V)CH_3$;
A is N or CH;
V is O or NH;
$R_4$ and $R_5$ are independently selected from hydrogen and substituted or unsubstituted alkyl and aryl groups and Q is substituted or unsubstituted aryl groups.

12 Claims, No Drawings

PYRIDAZINONES AND THEIR USE AS FUNGICIDES

This application is a divisional application of application Ser. No. 08/660,244 filed Jun. 7, 1996, now U.S. Pat. No. 5,763,440, which was a continuation of application Ser. No. 08/337,712 filed Nov. 14, 1994, now abandoned.

This invention relates to pyridazinones and related compounds, compositions containing these compounds and methods for controlling fungi by the use of a fungitoxic amount of these compounds.

European Patent Application No. 0 478 195 A1 published Apr. 1, 1992, entitled "Dihydropyridazinones, Pyridazinones and Related Compounds and Their Use As Fungicides" discloses pyridazinone compounds as effective fungicides. The present inventions are novel compositions which have also been discovered to possess fungicial properties.

The pyridazinones of the present invention have the formula I

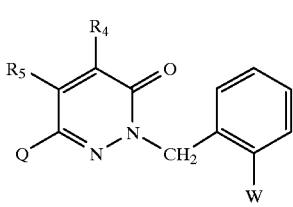

(I)

wherein W is $CH_3$—O—A=C(-)—CO(V)$CH_3$; A is N or CH; V is O or NH; and $R_4$ and $R_5$ are independently selected from hydrogen, $(C_1-C_8)$alkyl, $(C_1-C_8)$alkoxy, cyano, halo $(C_1-C_{12})$alkyl, $(C_2-C_8)$alkenyl, $(C_3-C_{10})$alkynyl, aryl and aralkyl where the aforementioned $(C_1-C_8)$alkoxy, $(C_1-C_8)$alkyl, $(C_2-C_8)$alkenyl and $(C_3-C_{10})$alkynyl groups may be optionally substituted with up to three substituents selected from the group consisting of halogen, nitro and trihalomethyl;

Q is selected from the group having the following formula:

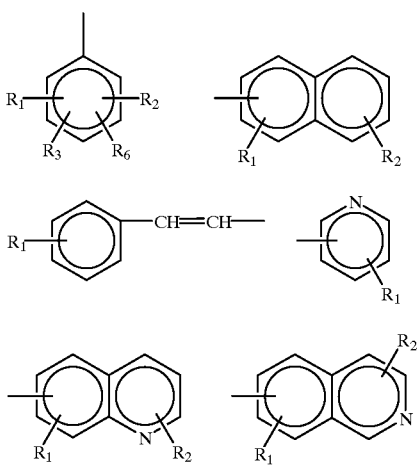

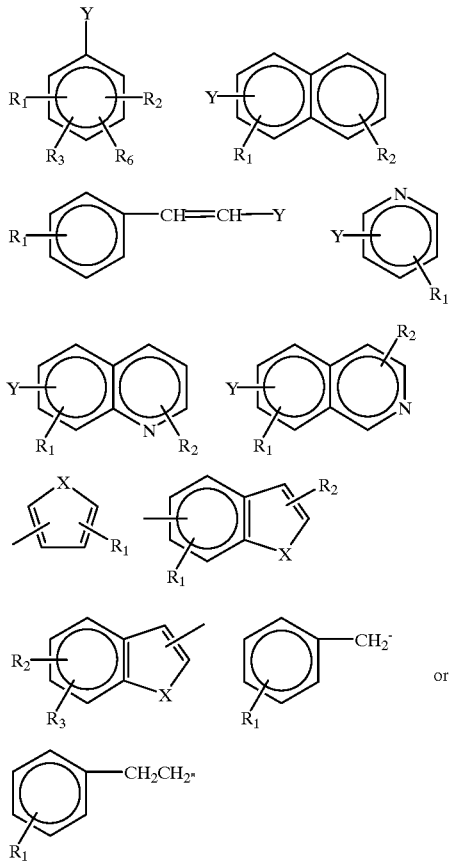

where Y is O or S and forms a direct bond to the pyridazine ring and where $R_3$ and $R_6$ are independently selected from hydrogen, halogen, cyano, nitro, trihalomethyl, methyl, phenyl, phenoxy, $(C_1-C_4)$alkyl which may be substituted with up to 3 halogen atoms, $(C_1-C_4)$-alkylthio, $(C_1-C_4)$alkylsulfoxide and $(C_1-C_{18})$alkoxy;

$R_1$ and $R_2$ are independently selected from hydrogen, $(C_1-C_4)$alkyl, $(C_1-C_4)$alkoxy, halogen, cyano, nitro; and X is O, or S.

The aforementioned $(C_1-C_{12})$alkyl, $(C_2-C_8)$alkynyl and $(C_3-C_{10})$alkynyl groups may be optionally substituted with up to three substituents selected from the group consisting of halogen, nitro, trihalomethyl and cyano.

The term alkyl includes both branched and straight chained alkyl groups, such as methyl, ethyl, n-propyl, isopropyl, n-butyl, sec-butyl, isobutyl, t-butyl, n-pentyl, isopentyl, n-hexyl, n-heptyl, isooctyl nonyl, decyl undecyl, dodecyl and the like. Haloalkyl is defined as an alkyl group substituted with 1 to 3 halogens.

The term "alkenyl" refers to an ethylenically unsaturated hydrocarbon group, straight or branched, having a chain length of 2 to 8 carbon atoms and 1 or 2 ethylenic bonds. The term haloalkenyl refers to an alkenyl group substituted with 1 to 3 carbon atoms. The term "alkynyl" refers to an unsaturated hydrocarbon group, straight or branched, having a chain length of 2 to 12 carbon atoms and 1 or 2 acetylenic bond.

The term "aryl" includes phenyl or napthyl, which maybe substituted with up to three substituents selected from the group consisting of halogen, cyano, nitro, trihalomethyl, methyl, phenyl, phenoxy, optionally substituted halo-substituted ($C_1$–$C_4$)alkyl, ($C_1$–$C_4$)alkylthio, ($C_1$–$C_4$)alkylsulfoxide and ($C_1$–$C_{18}$)alkoxy.

Typical aryl substituents include but are not limited to 4-chlorophenyl, 4-fluorophenyl, 4-bromophenyl, 2-methoxyphenyl, 2,4-dibromophenyl, 3,5-diflourophenyl, 2,4,6-trichlorophenyl, 4-methoxyphenyl, 2-chloronapthyl, 2,4-dimethoxphenyl, 4-(trifluormethyl)phenyl, 2,4-diiodonapthyl, 2-iodo-4-methylphenyl.

The term "aralkyl" is used to describe a group wherein the the alkyl chain is from 1 to 5 carbon atoms and can be branched or straight chain, preferably a straight chain, with the aryl portion as defined above. Typical aralkyl substituents include but are not limited to 2,4-dichlorobenzyl, 2,4-dibromobenzyl, 2,4,6-trichlorobenzyl, 3,5-dimethoxyphenethyl, 2,4,5-trimethylphenbutyl, 2,4-dibromonapthylbutyl, 2,4-dichlorophenylethyl and the like.

Halo is meant to include iodo, fluoro, bromo and chloro moieties.

Because of the C=C or C=N double bonds the novel compounds of the general formula I nay be obtained in preparation as E/Z isomeric mixtures. These isomers can be separated into individual components by conventional means. Both the individual isomeric compounds and mixtures thereof form subjects of the invention and can be used as fungicides.

A preferred embodiment of this invention are the compounds, enantiomorphs, salts and complexes of Formula (I) is when $R_4$ and $R_5$ are hydrogen and Q is is phenyl or phenyl-substituted with preferably two substituents independently selected from halo, trihalomethyl, cyano, ($C_1$–$C_4$) alkyl, ($C_1$–$C_4$)alkylthio, ($C_1$–$C_4$)alkoxy or phenyl.

A more preferred embodiment of this invention are the compounds, entiamorphs, salts and complexes of Formula (I) is when $R_4$ and $R_5$ are hydrogen Q is phenyl, or phenyl substituted at the 3 or 4 position or 3,4 positions with halo and when A is CH, V is O and when A is N, V is O or NH. The preferred geometry when A is CH or N is the E isomer.

Typical compounds of Formula (I) encompassed by the present invention include those compounds presented in Table 1 below:

TABLE 1

| Compound # | Q | R-4 | R-5 | A | V |
|---|---|---|---|---|---|
| 1 | 2CN(AR) | H | H | CH | O |
| 2 | 2NO$_2$(AR) | H | H | CH | O |
| 3 | 2ARO(AR) | H | H | CH | O |
| 4 | 2,3-Cl$_2$(AK) | H | H | CH | O |
| 5 | 2CH$_3$(AR) | H | H | CH | O |
| 6 | 4NO$_2$(AR) | H | H | CH | O |
| 7 | ARCH$_2$— | H | H | CH | O |
| 8 | 2Cl(AR)CH$_2$— | H | H | CH | O |
| 9 | 3Cl(AR)CH$_2$— | H | H | CH | O |
| 10 | 4Cl(AR)CH$_2$— | H | H | CH | O |
| 11 | 3,4Cl(AR)CH$_2$— | H | H | CH | O |
| 12 | 4Br(AR)CH$_2$— | H | H | CH | O |
| 13 | 3,5Cl(AR)CH$_2$— | H | H | CH | O |
| 14 | 2CN(AR)CH$_2$— | H | H | CH | O |
| 15 | (AR)CH$_2$CH$_2$— | H | H | CH | O |
| 16 | 2Cl(AR)CH$_2$CH$_2$— | H | H | CH | O |
| 17 | 3Cl(AR)CH$_2$CH$_2$— | H | H | CH | O |
| 18 | 3,4Cl(AR)CH$_2$CH$_2$— | H | H | CH | O |
| 19 | 2CN(AR)CH$_2$CH$_2$— | H | H | CH | O |
| 20 | 2NO$_2$(AR) | H | H | N | O |
| 21 | 2ARO(AR) | H | H | N | O |
| 22 | 2Cl(AR) | H | H | N | O |
| 23 | 3Cl(AR) | H | H | N | O |

TABLE 1-continued

| Compound # | Q | R-4 | R-5 | A | V |
|---|---|---|---|---|---|
| 24 | 4Cl(AR) | H | H | N | O |
| 25 | 2CN(AR) | H | H | N | O |
| 26 | ARCH$_2$(AR) | H | H | N | O |
| 27 | 2Cl(AR)CH$_2$— | H | H | N | O |
| 28 | 3Cl(AR)CH$_2$— | H | H | N | O |
| 29 | 4Cl(AR)CH$_2$— | H | H | N | O |
| 30 | 2CN(AR)CH$_2$— | H | H | N | O |
| 31 | ARCH$_2$CH$_2$ | H | H | N | O |
| 32 | 2Cl(AR)CH$_2$CH$_2$— | H | H | N | O |
| 33 | 3Cl(AR)CH$_2$CH$_2$— | H | H | N | O |
| 34 | 4Cl(AR)CH$_2$CH$_2$— | H | H | N | O |
| 35 | 2CN(AR)CH$_2$CH$_2$— | H | H | N | O |
| 36 | 2NO$_2$(AR) | H | H | N | NH |
| 37 | 2ARO(AR) | H | H | N | NH |
| 38 | 2Cl(AR) | H | H | N | NH |
| 39 | 3Cl(AR) | H | H | N | NH |
| 40 | 4Cl(AR) | H | H | N | NH |
| 41 | 2CN(AR) | H | H | N | NH |
| 42 | 3CN(AR) | H | H | N | NH |
| 43 | 2Br(AR) | H | H | N | NH |
| 44 | 3Br(AR) | H | H | N | NH |
| 45 | 4Br(AR) | H | H | N | NH |
| 46 | 4CN(AR) | H | H | N | NH |
| 47 | 2F(AR) | H | H | N | NH |
| 48 | 3F(AR) | H | H | N | NH |
| 49 | 4F(AR) | H | H | N | NH |
| 50 | 2Cl(AR)CH$_2$— | H | H | N | NH |
| 51 | 3Cl(AR)CH$_2$— | H | H | N | NH |
| 52 | 4Cl(AR)CH$_2$— | H | H | N | NH |
| 53 | 2CN(AR)CH$_2$ | H | H | N | NH |
| 54 | 2Cl(AR)CH$_2$CH$_2$— | H | H | N | NH |
| 55 | 3Cl(AR)CH$_2$CH$_2$— | H | H | N | NH |
| 56 | 4Cl(AR)CH$_2$CH$_2$— | H | H | H | NH | where AR is understood to be phenyl.

The pyridazinones of the of the present invention may be prepared by conventional synthetic routes. For example when A in Formula (I) is CH and V is O the compounds may be prepared as shown by scheme A:

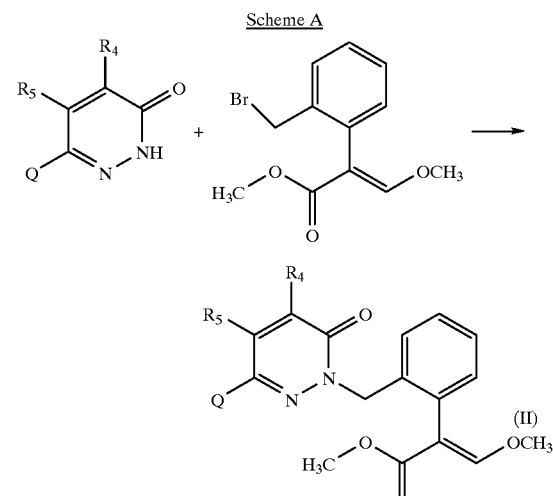

Scheme A

The reaction of 4,5,6-trisubstituted-3(2H)-pyridazinones with methyl E-a-(2-bromomethylphenyl)-b-methoxyacrylate is carried out in the presence of a base such as a metal hydride, preferably NaH, in an aprotic solvent such as N,N-dimethyl-formamide. 4,5,6-trisubstituted-3 (2H)-pyridazinones can be prepared as described in EP 308404 now U.S. Pat. No. 5,552,409. Methyl E-a-(2- bromomethylphenyl)-b-methoxyacrylate, as a single E isomer, can be prepared in two steps from 2-methylphenylacetate as described previously in U.S. Pat. No. 4,914,128. Alternatively, shown in Scheme B the 4,5,6-trisubstituted-3(2H)-pyridazinones can be reacted with methyl 2-(bromomethyl)phenyl glyoxylate followed by Wittig condensation with methoxymethyltriphenylphosphorane as described in EP 348766 now U.S. Pat. No. 5,041,618; EP178826 now U.S. Pat. No. 5,315,025; and DE 3705389 now U.S. Pat. No. 4,937,372.

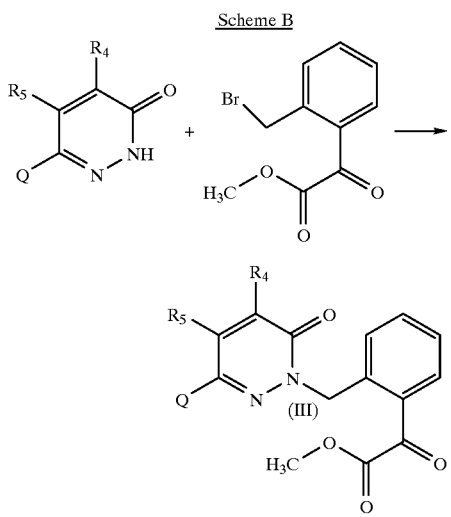

When A in Formula (I) is N and V is O the compounds may be prepared as shown by scheme C:

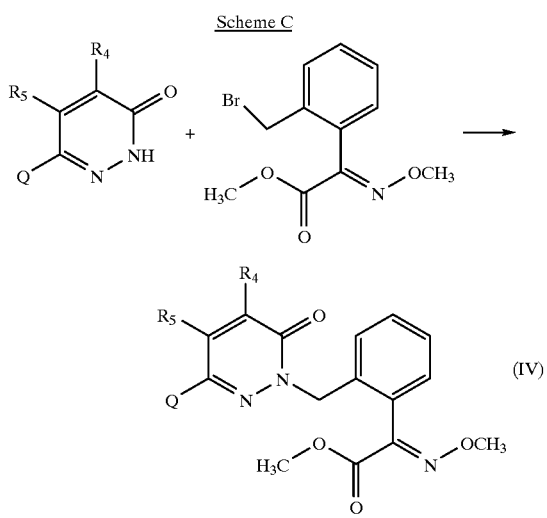

The reaction of 4,5,6-trisubstituted-3(2H)-pyridazinones with methyl E-2-(bromomethyl)phenylglynoxylate O-methyloxime is carried out in the presence of a base such as a metal hydride, preferably NaH, in an aprotic solvent such as N,N-dimethylformamide. Methyl 2-(bromomethyl) phenylglyoxylate O-methyloxime can be prepared as described in U.S. Pat. Nos. 4,999,042 and 5,157,144. Methyl 2-methylphenylacetate is treated with an alkyl nitrite under basic conditions to provide after methylation methyl 2-methylphenylglyoxalate O-methyl oxime which can also be prepared from methyl 2-methylphenylglyoxalate by treatment with 2-hydroxylamine hydrochloride and methylation or by treatment with methoxylamine hydrochloride. Alternatively, as in shown in Scheme D the 4,5,6-trisubstituted-3(2H)-pyridazinones can be reacted with methyl 2-(bromomethyl)-phenylglyoxylate followed by reaction with methoxylamine hydrochloride or hydroxylamine hydrochloride followed by methylation.

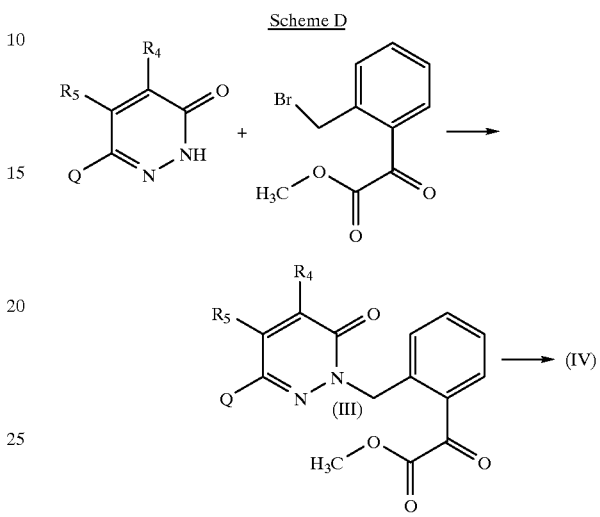

Similarly, when A in Formula (I) is N, the compounds may be prepared by Scheme E:

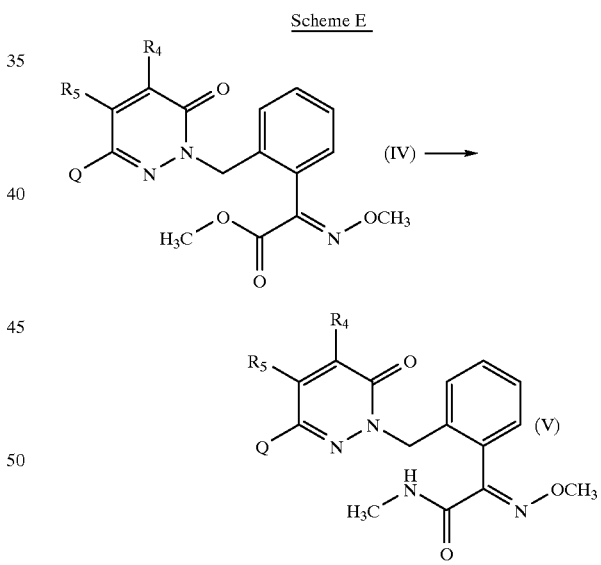

The amminolysis of oximinoacetates to oximinoacetamides has been described in U.S. Pat. Nos. 5,185,342, 5,221,691 and 5,194,662. In scheme E 2-methoxyiminoactetates (IV) of the present invention are treated with 40% aqueous methylamine in methanol and provides 2-methoxyiminoacetamides (V). Alternatively, in scheme F, 4,5,6-trisubstituted-3(2H)-pyridazinones are reacted with N-methyl E-2- methoxyimino-2-[2-(bromomethyl)phenyl] acetamide in the presence of a base such as a metal hydride, preferably NaH, in an aprotic solvent such as dimethly formide (DMF). N-methyl E-2-methoxyimino-2-[2-(bromomethyl)phenyl]acetamide is described in WO 9419331. More specifically N-methyl E-2-methoxyimino-2-[2-(bromomethyl)phenyl]-acetamide is prepared from the corresponding arloxy compound by cleavage with hydrogen bromide in inert solvents such as halogenated hydrocarbon at −30° C. to 40° C. In addition the chloromethyl analog is prepared by cleavage with boron trichloride under similar conditions.

Another route to the methoxyimino acetamide (VI) is described in U.S. Pat. No. 5,381,714, see in particular column 13.

Scheme B, on page 6 herein), by amminolysis with 40% aqueous methylamine in anhydrous methanol with stirring at room temperature. The resulting ketoamide is treated with methoxylamine HCl in methanol at reflux to provide the methoximino acetamide (V) or with hydroxylamine HCl in methanol at reflux followed by methylation with dimethylsulfate in acetone at room temperature.

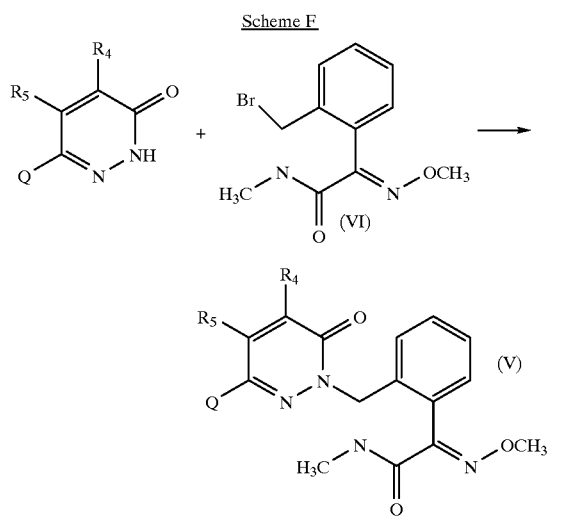

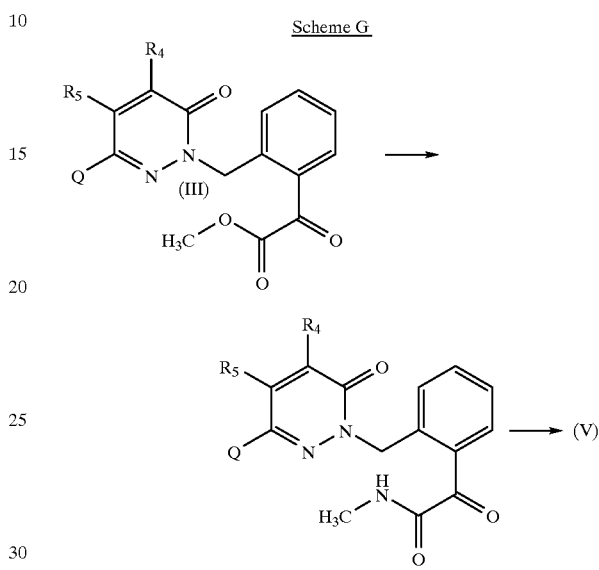

Finally, as described in EP 585751 and the corresponding Canadian Patent 2,104,806, and as shown in Scheme G, the oximinoacetamide (V) can be formed from the keto ester (III) (as previously formed by the reaction depicted in The following examples of Formula (I) in Table 2 are provided to illustrate the present invention.

TABLE 2

| Compound # | Q | R-4 | R-5 | A | V |
|---|---|---|---|---|---|
| 57 | 4Cl(AR) | H | H | CH | O |
| 58 | 2CH$_3$(AR)-O | H | H | CH | O |
| 59 | 3CH$_3$(AR)-O | H | H | CH | O |
| 60 | 4CH$_3$(AR)-O | H | H | CH | O |
| 61 | 2Cl(AR)-O | H | H | CH | O |
| 62 | 3Cl(AR)-O | H | H | CH | O |
| 63 | 4Cl(AR)-O | H | H | CH | O |
| 64 | 2CN(AR)-O | H | H | CH | O |
| 65 | 3CN(AR)-O | H | H | CH | O |
| 66 | 3ClAR(AR) | H | H | CH | O |
| 67 | AR | AR | CN | CH | O |
| 68 | 4Br(AR) | H | H | CH | O |
| 69 | 3,5Cl(AR) | H | H | CH | O |
| 70 | 3,4Cl(AR) | H | H | CH | O |
| 71 | 4F(AR) | H | H | CH | O |
| 72 | 4SCH$_3$(AR) | H | H | CH | O |
| 73 | 4SO$_2$CH$_3$(AR) | H | H | CH | O |
| 74 | 3CH(AR) | H | H | CH | O |
| 75 | 2-NAPTHYL | H | H | CH | O |
| 76 | 3,4Cl(AR) | H | H | N | O |
| 77 | AR | H | H | CH | O |
| 78 | 3,4Cl(AR) | H | H | N | NH |
| 79 | 3-THIENYL | H | H | CH | O |
| 80 | 4-AR(AR) | H | H | CH | O |
| 81 | 4OCH$_3$(AR) | H | H | CH | O |
| 82 | 4ARO(AR) | H | H | CH | O |
| 83 | 1-NAPTHYL | H | H | CH | O |
| 84 | 2OC$_2$H$_5$,5C$_3$H$_7$(AR) | H | H | CH | O |
| 85 | 2CF$_3$(AR) | H | H | CH | O |
| 86 | 4OCH$_3$-1-NAPTHYL | H | H | CH | O |
| 87 | 2OC$_{18}$H$_{37}$,5C$_3$H$_7$(AR) | H | H | CH | O |

TABLE 2-continued

| Compound # | Q | R-4 | R-5 | A | V |
|---|---|---|---|---|---|
| 88 | 3CF$_3$(AR) | H | H | CH | O |
| 89 | 3NO$_2$(AR) | H | H | CH | O |
| 90 | 3ARO(AR) | H | H | CH | O |
| 91 | 3CN(AR) | H | H | CH | O |
| 92 | 4CN(AR) | H | H | CH | O |
| 93 | 3CH$_3$(AR) | H | H | CH | O |
| 94 | AR | CH$_2$(3-THIENYL) | H | CH | O |
| 95 | 2-THIENYL | CH$_2$AR(3,4Cl) | H | CH | O |
| 96 | 2-THIENYL | AR | H | CH | O |
| 97 | 2-THIENYL | CH$_2$AR(3CF$_3$) | H | CH | O |
| 98 | 4Cl(AR) | H | C$_4$H$_9$ | CH | O |
| 99 | 5Br-2-THIENYL | H | H | CH | O |
| 100 | 2OH(AR) | H | H | CH | O |
| 101 | 2-PYRIDYL | H | H | CH | O |
| 102 | 3-PYRIDYL | H | H | CH | O |
| 103 | 2OCH$_3$(AR) | H | H | CH | O | where AR is understood to be phenyl.

The compounds of this invention can be made according to the following procedures:

EXAMPLE 1

Preparation of Methyl a-[2-(6'-(4"-chlorophenyl)pyridazin-3'-on-2'-yl)-methylphenyl]-b-methoxyacrylate. (Table 2, Compound 57)

To a dry 100 ml three neck flask equipped with magnetic stirrer, nitrogen inlet, and pressure equalized side-arm addition funnel was charged 0.3 g (7.3 mmoles) of 60% sodium hydride oil suspension and 10 mls of dry dimethylformamide. A solution of 1.5 g (7.3 mmoles) of 6-(4-chlorophenyl)-3(2H)-pyridazinone in 20 mls of dimethylformamide was added dropwise at ambient temperature. The solution was stirred for 1 hour at room temperature. A solution of 2.1 g (7.3 mmoles) of methyl a (bromomethylphenyl)-b-methoxyacrylate in 20 mls of dimethylformamide was added dropwise at room temperature, and the reaction was stirred under nitrogen at ambient temperature for a total of 2 hours. The reaction was then quenched with 100 mls of water, and extracted with ethyl acetate (3×100 mls). The organic extract was washed with 100 mls of water, 100 mls of saturated sodium chloride solution, dried over anhydrous magnesium sulfate and filtered. The filtrate was concentrated by evaporation under reduced pressure to afford 2.1 g of the title compound as a thick yellow oil.

EXAMPLE 2

Preparation of Methyl 2-[2-(6'-(3",4"-dichlorophenyl)pyridazin-3'-on-2'-yl)-methylphenyl]-2-methoxyiminoacetate. (Table 2. Compound 76)

To a dry 100 mls three neck flask equipped with magnetic stirrer, nitrogen inlet, and pressure equalized side-arm addition funnel was charged 0.17 g (4.15 mmoles) of 60% sodium hydride oil suspension and 10 mls of dry dimethylformamide. A solution of 1.0 g (4.15 mmoles) of 6-(3,4-dichlorophenyl)-3(2H)-pyridazinone in 20 mls of dimethylformamide was added dropwise at ambient temperature. A solution was stirred for 1 hour at room temperature. A solution of 1.2 g (4.15 mmoles) of methyl 2-bromomethylphenylglyoxylate O-methyloxime in 20 mls of dimethylformamide was added dropwise at room temperature, and the reaction was stirred under nitrogen at ambient temperature for a total of 3 hours. The reaction was then quenched with 100 mls of water, and extracted with ethyl acetate (3×100 mls). The organic extract was washed with 100 mls of water, 100 mls of saturated sodium chloride solution, dried over anhydrous magnesium sulfate and filtered. The filtrate was concentrated by evaporation under reduced pressure to afford 1.6 g of a dark liquid which was chromatographed on silica gel with 100% ethyl acetate to afford 1.2 g of the title compound as a thick, pale yellow liquid.

EXAMPLE 3

Preparation of N-Methyl 2-[2-(6'-(3",4"-dichlorophenyl)pyridazin-3'-on-2'-yl)methylphenyl]-2-methoxyiminoacetamide. (Table 2, Compound 78)

To a 50 ml flask equipped with magnetic stirrer was charged 0.5 g of methyl 2-[2-(6'-(3",4"-chlorophenyl)pyridazin-3'-on-2'-yl)methylphenyl]-2-methoxyiminoacetate (1.12 mmoles) and 20 mls of anhydrous methanol. With stirring, 0.5 mls of 40% aqueous methyl amine was added to the methanol solution, and the reaction was stirred at ambient temperature for a total of 48 hours. The solution was then concentrated by evaporation under reduced pressure, and the residue was dissolved in 100 mls of ethyl acetate. The organic extract was washed with 100 mls of water and 100 mls of saturated sodium chloride solution, dried over anhydrous magnesium sulfate, and filtered. The filtrate was concentrated by evaporation under reduced pressure to afford 0.5 g of the product as a light brown solid.

EXAMPLE 4

NMR data (200MHz) are provided for the compounds provided in Table 2.

| Compound# | 1H NMR (CDCl3),TMS = 0 ppm: |
|---|---|
| 57 | 3.6(s,3H), 3.8(s,3H), 5.3(s,2H), 6.9(d,1H), 7.1(m,1H), 7.2–7.5(m,5H), 7.55–7.8(m,4H) |
| 58 | 2.0(s3,H),3.6(s,3H), 3.8(s,3H), 4.7–5.3.(bs,2H), 6.9(m,2H), 7.1–7.4(m,8H), 7.5(s,1H) |
| 59 | 2.3(s,3H), 3.6(s,3H), 3.8(s,3H), 4.4–5.4.(bd,2H), 6.8(m,2H), |

| Compound# | 1H NMR (CDCl3),TMS = 0 ppm: |
|---|---|
| | 6.9–7.3(m,8H), 7.5(s,1H) |
| 60 | 2.4(s,3H), 3.6(s,3H), 3.8(s,3H), 4.5–5.4.(bd,2H), 6.8–7.4(m,10H), 7.5(s,1H) |
| 61 | 3.6(s,3H), 3.8(s,3H), 4.6–5.3.(bs,2H), 6.9(d,1H), 7.0–7.3(m,8H), 7.4(m,1H), 7.5(s,1H) |
| 62 | 3.6(s,3H), 3.8(s,3H), 4.5–5.5.(bd,2H), 6.9(m,1H), 7.0(d,1H), 7.1–7.4(m,8H), 7.5(s,1H) |
| 63 | 3.6(s,3H), 3.8(s,3H), 4.5–5.5.(bd,2H), 6.8–7.1(m,4H), 7.1–7.4(m,6H), 7.5(s,1H) |
| 64 | 3.6(s,3H), 3.8(s,3H), 4.4–5.6.(bd,2H), 6.9–7.4(m,8H), 7.5(s,1H)7.6–7.8(m,2H) |
| 65 | 3.6(s,3H), 3.8(s,3H), 4.4–5.6.(bd,2H), 7.0(q,2H), 7.1–7.4(m,8H) 7.5(m,1H) |
| 66 | 3.6(s,3H), 3.8(s,3H), 5.4(bs,2H), 7.0(d.1H), 7.2(m,1H) 7.35(m,2H), 7.4–7.5(m,3H), 7.5–7.6(m,3H) |
| 67 | 3.6(s,3H), 3.8(i,3H), 5.0–5.8(bd,2H), 6.9(d,2H), 7.1–7.3(m,6H) 7.35–7.5(m,5H), 7.6(s,2H) |
| 68 | 3.6(s,3H), 3.8(s,3H), 5.4(bs,2H), 7.0(d,1H), 7.15(m,1H), 7.3(m,2H), 7.45(m,1H), 7.5–7.6(m,6H) |
| 69 | 3.6(s,3H), 3.8(s,3H), 5.4(bs,2H), 7.0(d,1H), 7.2(m,1H), 7.3–7.5(m 4H), 7.55–7.7(m,4H) |
| 70 | 3.6(s,3H), 3.8(s,3H), 5.4(bs,2H), 7.0(d,1H), 7.2(m,1H), 7.3–7.7(m,7H), 7.8(s,1H) |
| 71 | 3.6(s,3H), 3.8(s,3H), 5.4(bs,2H), 7.0–7.25(m,4H), 7.3–7.5(m,3H), 7.6–7.8(m,4H) |
| 72 | 2.5(s,3H), 3.6(s,3H), 3.8(s,3H), 5.4(bs,2H), 7.0(d,1H), 7.1–7.5(m,6H), 7.55–7.8(m,4H) |
| 73 | 3.1(s,3H), 3.6(s,3H), 3.8(s,3H), 5.3(bs,2H), 7.0(d,1H), 7.1–7.5(m,4H),7.6(s,1H), 7.7(d,1h), 7.8–8.1(m,4H) |
| 74 | 3.6(s,3H), 3.8(s,3H), 5.4(bs,2H), 7.0(d,1H), 7.1(m,1H), 7.3–7.5(m,6H), 7.55–7.9(m,3H) |
| 75 | 3.6(s,3H), 3.8(s,3H), 5.4(bs,2H), 7.0(d,1H), 7.1(m,1H), 7.35(m,2H), 7.5(m,3H), 7.6(s,1H), 7.8(d,1H), 7.9(m,4H),8.1(s,1H) |
| 76 | 3.8(s,3H), 4.1(s,3H), 5.3(s,2H), 7.0(d,1H), 7.2(m,1H), 7.4(m,2H), 7.6(m,5H), 7.9(s,1H) |
| 77 | 3.6(s,3H), 3.8(s,3H), 5.4(bs,2H), 7.0(d,1H), 7.2(m,1H), 7.3–7.4(m,2H), 7.45–7.6(m,5H), 7.6(s,1H), 7.7–7.85(m,2H) |
| 78 | 2.9(d,3H), 3.9(s,3H), 5.3(s,2H), 7.0(m,2H), 7.2(m,1H), 7.4(m,2H), 7.5–7.7(m,4H), 7.9(s,1H) |
| 79 | 3.6(s,3H), 3.8(s,3H), 5.3(s,2H), 7.0(d,1H), 7.2(m,1H), 7.3–7.7(m,8H) |
| 80 | 3.6(s,3H), 3.8(s,3H), 5.3(s,2H), 7.0(d,1H), 7.2(m,1H), 7.3–7.9(m,14H) |
| 81 | 3.6(s,3H), 3.8(s,3H), 3.9(s,3H), 5.3(s,2H), 7.0(m,3H), 7.2(m,1H), 7.3(m,2H), 7.4(m,1H), 7.5–7.7(m,4H) |
| 82 | 3.6(s,3H), 3.8(s,3H), 5.3(s,2H), 7.0–7.2(m,6H), 7.3–7.5(m,5H), 7.6–7.8(m,5H) |
| 83 | 3.5(s,3H), 3.8(s,3H), 4.9–5.8(bd,2H), 7.0(d,1H), 7.2–7.6(m,11H), 7.8–7.95(m,2H) |
| 84 | 0.9(t,3H), 1.4(t,3H), 1.6(q,3H), 2.5(t,2H), 3.6(s,3H), 3.9(s,3H), 4.0(q,2H), 5.3(s,2H), 6.9(m,2H), 7.1–7.5(m,6H), 7.6(s,1H), 7.7(d,1H) |
| 85 | 3.6(s,3H), 3.8(s,3H), 5.4(s,2H), 7.0(d,1H), 7.2(m,1H), 7.3(m,2H), 7.4–7.7(m,5H), 7.9(d,1H), 8.0(s,1H) |
| 86 | 3.5(s,3H), 3.8(s,3H), 4.0(s,3H), 4.9–5.8(bd,2H), 7.0(d,1H), 7.2–7.7(m,10H), 7.8(d,1H), 8.2(d,1H) |
| 87 | 0.9–1.0(m,8H), 1.1–1.5(m,28H), 1.6–1.8(m,8H), 2.5(t,2H), 3.6(s,3H), 3 9(s,3H), 4.0(q,2H), 5.3(s,2H), 6.9(m,2H), 7.1–7.5(m,6H), 7.6(s,1H), 7.7(d,1H) |
| 88 | 3.6(s,3H), 3.8(s,3H), 5.4(s,2H), 7.0(d,1H), 7.2(m,1H), 7.3(m,2H), 7.4(m,1H), 7.5–7.7(m,4H), 7.9(d,1H), 8.0(s,1H) |
| 89 | 3.6(s,3H), 3.8(s,3H), 5.4(s,2H), 7.0(d,1H), 7.2(m,1H), 7.3(m,2H), 7.45(m,1H), 7.5–7.7(m,3H), 8.0(d,1H), 8.2(d,1H), 8.6(s,1H) |
| 90 | 3.6(s,3H), 3.8(s,3H), 5.4(s,2H) 6.9–7.7(m,16H) |
| 91 | 3.6(s,3H), 3.8(s,3H), 5.4(s,2H), 7.0(d,1H), 7.2(m,1H), 7.3(m,2H), 7.4(m,1H), 7.5–7.7(m,4H), 7.95(d,1H), 8.1(s,1H) |
| 92 | 3.6(s,3H), 3.8(s,3H), 5.3(s,2H), 7.0(d,1H), 7.2(m,1H), 7.3(m,2H), 7.4(m,1H), 7.5–7.9(m,6H) |
| 93 | 2.45(s,3H), 3.6(s,3H), 3.8(s,3H), 5.4(s,2H), 7.0(d,1H), 7.1–7.8(m,10H) |
| 94 | 3.5(s,3H), 3.7(s,3H), 4.0(s,2H), 5.35(s,2H), 7.0(m,1H), 7.1–7.5(m,10H), 7.6(m,3H) |
| 95 | 3.6(s,3H), 3.8(s,3H), 3.9(s,2H), 5.35(s,2H), 7.0(m,1H), 7.1–7.5(m,10H), 7.6(s,1H) |
| 96 | 3.6(s,3H)), 3.8(s,3H), 3.9(s,2H), 5.4(s,2H), 7.0–7.2(m,2H), 7.2–7.7(m,9H), 7.8(m,3H) |
| 97 | 3.6(s,3H), 3.8(s,3H), 4.0(s,2H), 5.35(s,2H), 7.0–7.7(m,13H) |
| 98 | 1.0(t,3H), 1.4(m,2H), 1.6(m,2H), 2.5(t,2H), 3.6(s,3H), 3.8(s,3H), 5.4(s,2H), 7.1(m,1H), 7.2–7.5(m,7H), 7.6–7.7(m,2H) |
| 99 | 3.7(s,3H), 3.9(s,3H), 5.35(s,2H), 6.9(d,1H), 7.1(t,2H), 7.2(m,1H), 7.3(m,3H), 7.45(d,1H), 7.6(s,1H) |
| 100 | 3.7(s,3H), 3.9(s,3H), 4.8–5.8(bs,2H), 6.9(m,2H), 7.1(d,1H), 7.2–7.7(m,7H), 7.8(d,1H), 10.0(s,1H) |
| 101 | 3.6(s,3H), 3.8(s,3H), 5.4(s,2H), 6.9(d,1H), 7.1–7.55(m,5H), 7.6(s,1H), 7.7(t,1H), 8.0(d,1H), 8.3(d,1H), 8.6(s,1H) |
| 102 | 3.6(s,3H), 3.8(s,3H), 5.3(s,2H), 6.9(d,1H), 7.15(m,1H), 7.3(m,4H), 7.4(m,1H) 7.6(s,1H), 8.0(d,1H), 8.6(s,1H), 9.0(s,1H) |
| 103 | 3.6(s,3H), 3.75(s,3H), 3.85(s,3H), 5.3(bs,2H), 6.8–7.1(m,4H), 7.2(m,1H), 7.25–7.5(m,4H), 7.6(s,1H), 7.7(d,1H) |

EXAMPLE 5

Numerous compounds of this invention were tested for fungicidal activity in vivo against the diseases described below. In tests on cereals (except rice plants used for testing rice blast), the plants were trimmed about 24 hours prior to the application of the fungicide compound to provide a uniform plant height and to facilitate uniform application of the compound and inoculation with the fungus. The compounds were dissolved in a 2:1:1 mixture of water, acetone and methanol, sprayed onto the plants, allowed to dry (four to six hours) and then the plants were inoculated with the fungus. Each test utilized control plants which were sprayed with the water, acetone and methanol mixture and inoculated with the fungus. The remainder of the technique of each of the tests is given below and the results are reported in Table 2 as percent disease control (percentages of plants treated with the compounds of the present invention lacking disease signs or symptoms compared to the untreated control plants). One hundred is rated as total disease control and zero as no disease control. The application of the fungi to the test plants is as follows:

Wheat Powdery Mildew (WPM)

*Erysiphe graminis* (f. sp. tritici) was cultured on wheat seedlings in a controlled temperature room at 65° to 70° F. Mildew spores were shaken from the culture plants onto wheat seedlings which had been previously sprayed with the fungicide compound. The inoculated seedlings were kept in a controlled temperature room at 65° to 75° F. and subirrigated. The percent disease control was rated 8 to 10 days after the inoculation.

Rice Blast (RB)

Nato rice plants were inoculated with Piricularia oryzae (about 20,000 conidia per ml) by spraying the leaves and stems with an airbrush until a uniform film of inoculum was observed on the leaves. The inoculated plants were incubated in a humid environment (75° to 85° F.) for about 24 hours, then placed in a greenhouse environment (70° to 75° F.). Seven to eight days after inoculation, the percent disease control was determined.

Wheat Leaf Rust (WLR)

*Puccinia recondita* (f. sp. tritici Races PKB and PLD) was cultured on 7 day old wheat (cultivar Fielder) over a 14 day period in the greenhouse. Spores were collected from the leaves with a cyclone vacuum or by settling on aluminum foil. The spores were cleaned by sieving through a 250 micron opening screen and stored or used fresh. Storage employed sealed bags in an Ultralow freezer. When stored, spores must be heat shocked for 2 minutes at 40° F. before use. A spore suspension is prepared from dry uredia by adding 20 mg (9.5 million spores) per mL of Soltrol oil. The suspension is dispensed into gelatin capsules (0.7 mL capacity) which is applied by DeVilbiss atomizer to the specimen plants. One capsule is used per flat of twenty of the 2 inch square pots of 7 day old Fielder wheat. After waiting for at least 15 minutes for the oil to evaporate from the wheat leaves, the plants are placed in a dark mist chamber (18–20° C. and 100% relative humidity) for 24 hours. The plants are then put in the greenhouse for the latent period and scored after 10 days for disease levels. For protective and curative tests, the plants are inoculated one day or two days, respectively, before spraying the plants with the fungicide compounds.

Cucumber Downy Mildew(CDM)

*Pseudoperonospora cubensis* was maintained on leaves of live Marketeer cucumber plants ina constant temperature room of 65 to 75° F. in humid air with moderate light intensity for 7 to 8 days. A water suspension of the spores from infested leaves was obtained and the spore concentration was adjusted to about $1\times10^5$ per ml of water. Marketeer cucumber seedlings were inoculated by spraying the underside of leaves with a DeVilbiss atomizer until small drops were observed on the leaves. The innoculated plants were incubated in a mist chamber for 24 hours at about 70° F. and subsequently incubated for 6 to 7 days in a controlled temperature roomunder mist at 65 to 75° F. Seven days after innoculation the percent disease control was determined.

Tomato Late Blight (TLB)

*Phytophthora infestans* was cultured on V8 juice plus $CaCO_3$ agar for three to four weeks. The spores were washed from the arag with water and sipsersed by DeVilbiss atomizer over the leaves of three week old Pixie tomato plants which had been sprayed previously with experimental fungicides. The inoculated plants were placed in a humidity cabinet at 20° C. for 24 hours for infection. The plants were then removed to a controlled environment room at 20° C. The plants were scored for disease control after five days.

Wheat Leaf Blotch (SNW)

*Septoria nodorum* was maintained on Czapek-Dox V-8 juice agar plates in an incubator in the dark at 20° C. for 48 to 72 hours, then incubated at 20° C. with alternating perios do 12 hours of light and 12 hours of darkness. A water suspension of the spores was obtained by shaking the portion of the plate with fungal material in deionized water and filtering through cheesecloth. The spore-containing water suspension was diluted to a spore concentration of $3.0\times10^6$ spores per ml. The inoculum was dispersed by a DeVilbiss atomizer over one week old Fielder wheat plants which had been previously sprayed with the fungicide compound. The inoculated plants were placed in a humidity cabinet at 20° C. with alternating 12 hours of light and 12 hours of darkness for 96 hours. The inoculated seedlings were then moved to a controlled environment room at 20° C. for 8 days of incubation. Disease control values were recorded as percent control.

Cucumber Powdery Mildew (CPM)

*Sphaerotheca fulginea* was maintained on cucumber plants, cv. Bush Champion, in the greenhouse. Inoculum was prepared by washing the spores from the leaves with water which had 1 drop of Tween 80 per 100 ml. After shaking the plants, the inoculum was filtered through cheese cloth and misted onto the plants with a squirt bottle mister. The plants were then placed in the greenhouse for infection and incubation. The plants were scored seven days after inoculation. Disease control values were recorded as percent control.

Grape Downy Mildew (GDM)

*Plasmopara Viticola* was maintained on leaves of live grape plants, cv. Delaware, in the controlled temperature chamber at 20° C. in humid air with moderate light intensity for 7 to 8 days. A water suspension of the spores from infested leaves was obtained and the spore concentration was adjusted to about $3\times10^5$ per ml of water. Delaware grape plants from tissue culture were inoculated by spraying the underside of leaves with a De Vilbiss atomizer until small drops were observed on the leaves. The inoculated plants were incubated in a mist chamber for 24 hours it 20° C. Disease control values were recorded as percent control seven days after inoculation.

Botrytis Gray Mold (BOT)

Several strains of *Botrytis cinerea* were maintained on PDA and were stored in closed plastic bosex at ambient temperature and room light for two to three weeks. A dextrose solution using 1.9 g/ 100 ml in tap water is used to wash the surface of the sporulating culture plates of the fungus. After the plates are rubbed with a rubber tipped spatula; the solution is poured through 2 layers of cheesecloth. A spore suspension of 5 to $6.5\times10^5$ spores per ml is sprayed on the upper and lower surfaces of Pixie tomato plants with a DeVilbiss atomizer. The plants are placed in a controlled temperature chamber with 100% RH at 20° C. with 12 hours of alternating light and darkness. Disease control values were recorded as percent control seven days after inoculation.

Tomato Early Blight (TEB)

*Alternaria solani* culture is produced using dried culture plates. The culture plates were covered with deionized water and scraped toloosen the spores. The solution of spores was filtered through two layers of cheesecloth. A final inoculum concentration of $8\times10^4$ spores per ml was used to inoculate the upper and lower surfaces of tomato plants, cv. San Marzano or Rutgers. The plants were placed in a humidity cabinet for 24 hours. Inoculated plants were removed from the humidity cabinet and placed in a greenhouse for seven to eight days. Efficacy values were recorded as percent control.

TABLE 3

| Cmpd # | DOSE (g/ha) | BOT | CDM | GDM | RB | SNW | TLB | WLR | WPM | CPM | TEB |
|---|---|---|---|---|---|---|---|---|---|---|---|
| 57 | 300 | 75(75) | 95 | 99 | 50 | 80 | 85 | 80 | 0 | 50 | 95 |
| 58 | 300 | 0 | 25 | 50 | 0 | 0 | | 0 | 0 | 0 | 0 |
| 59 | 300 | 0 | 60 | 50 | 0 | 0 | | 0 | 0 | 0 | 0 |
| 60 | 300 | 0 | 0 | 50 | 0 | 0 | | 0 | 0 | 0 | 0 |
| 61 | 300 | 50 | 0 | 75 | 0 | 0 | | 0 | 0 | 0 | |
| 62 | 300 | 0 | 0 | 50 | 0 | 0 | | 0 | 0 | 0 | |
| 63 | 300 | 0 | 0 | 95 | 0 | 50 | | 80 | 0 | 0 | |
| 64 | 300 | 50 | 0 | 0 | 0 | 0 | | 0 | 0 | 0 | |
| 65 | 300 | 0 | 0 | 0 | 0 | 0 | | 0 | 50(75) | 50 | |
| 66 | 300 | 50 | 95 | 75 | 0 | | 0 | | 0 | 0 | 0 |
| 67 | 300 | 50(75) | 95 | 50 | 0 | 0 | 0 | 50 | 0 | 0 | 0 |
| 68 | 300 | 90 | 100 | 75 | 50 | 90 | 75 | 95 | 0 | 90 | 60 |
| 69 | 300 | 90 | 100 | 50 | 90 | 90 | 0 | 90 | 0 | 50 | 75 |
| 70 | 300 | 90 | 100 | 99 | 90 | 95 | 50 | 90 | 50 | 75(75) | 80 |
| 71 | 300 | 75 | 85 | 90 | 90(75) | 90 | 50 | 95 | 75 | 85 | 75 |
| 72 | 300 | 75 | 90 | 75 | 80 | 90 | 0 | 90 | 0 | 50 | 0 |
| 73 | 300 | 75 | 0 | 0 | 0 | 0 | 0 | 95 | 0 | 0 | |
| 74 | 300 | 95 | 80 | 95 | 90 | 100 | 85 | 99 | 50 | 100 | 60 |
| 75 | 300 | 50(75) | | 100 | 50 | 0 | 0 | 90 | 75 | 0 | |
| 76 | 300 | 0 | | 0 | 0 | 0 | 0 | 0 | 0 | 0 | |
| 77 | 300 | 0 | | 95 | 50 | 80 | 0 | 50 | 0 | 75 | |
| 78 | 300 | 0 | | 0 | 0 | 0 | 0 | 0 | 0 | 0 | |
| 79 | 300 | 0 | | 75 | 0 | 0 | 0 | 0 | 0 | 50 | |
| 80 | 300 | 50 | | 50(75) | 0 | 80 | 0 | 0 | 0 | 0 | |
| 81 | 300 | 0 | | 50 | 0 | 50 | 0 | 0 | 0 | 0 | |
| 82 | 300 | 75(75) | | 50 | 0 | 0 | 0 | 0 | 50 | | |
| 83 | 300 | 50 | | 0 | 0 | 0 | 75 | 75 | 0 | | |
| 84 | 300 | 50 | | 90 | 0 | 0 | 50(75) | 0 | 0 | | |
| 85 | 300 | 50 | | 90 | 0 | 0 | 0 | 0 | 85 | | |
| 86 | 300 | 50 | | 90 | 0 | 0 | 75 | 0 | 50 | | |
| 87 | 300 | 0 | | 90 | 0 | 0 | 0 | 0 | 0 | 0 | |
| 88 | 300 | 50 | | 75 | 50 | 0 | 0 | 75 | 50 | 0 | |
| 89 | 300 | 0 | | 75 | 0 | 0 | 0 | 75 | 50 | 50 | |
| 90 | 300 | 0 | | 75 | 0 | 0 | 0 | 0 | 0 | 0 | |
| 91 | 300 | 0 | | 50 | 0 | 0 | 0 | 0 | 0 | 0 | |
| 92 | 300 | 0 | 50(75) | | 0 | 0 | 50 | 0 | 0 | 0 | |
| 93 | 300 | 50 | 50 | | 0 | 0 | 50 | 0 | 0 | 0 | |
| 94 | 300 | 50 | 100(75) | | 0 | 0 | 75 | 0 | 0 | 0 | |
| 95 | 300 | 50(75) | 0 | | 0 | 0 | 0 | 0 | 0 | 0 | |
| 96 | 300 | 0 | 25 | | 0 | 50 | 50 | 0 | 0 | 0 | |
| 97 | 300 | 50 | 75 | | 0 | 0 | s0 | 0 | 0 | 0 | |
| 98 | 300 | 0 | | 75(75) | 0 | 0 | 0 | 50 | 0 | 0 | |
| 99 | 300 | 0 | | 95 | 50 | 90 | 75 | 95 | 0 | 0 | |
| 100 | 300 | 0 | | 75(75) | 0 | 0 | 0 | 0 | 0 | 0 | |
| 101 | 300 | 50 | | 0 | 0 | 0 | 0 | 0 | 0 | 0 | |
| 102 | 300 | 50 | | 0 | 0 | 0 | 50 | 0 | 0 | 50 | |
| 103 | 300 | 50(75) | 95 | 0 | 0 | 0 | 0 | 0 | 0 | 0 | |

The symbol (75) indicates that the testing was performed at 75 g/ha.

The pyridazinones and the enantiomorphs, acid addition salts and metal salt complexes thereof are useful as agricultural fungicides and, as such, can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants are references, such as in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually, from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a pyridazinone, 45 parts of a synthetic precipitated hydrated silicon dioxide, such as that sold under the trademark Hi-SilR, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex®7.

Dusts are prepared by mixing the pyridazinone, or the enantiomorphs, salts and complexes thereof with finely divided inert solids which can be organic or inorganic in nature. Materials useful for this purpose include botanical flours, silicas silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The pyridazinones, and the enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.05 pound to about 50 pounds per acre and preferably from about 5 to about 25 pounds per acre of the active ingredient.

As a seed protectant, the amount of toxicant coated on the seed is usually at a dosage rate of from about 0.05 to about 20, preferably from about 0.05 to about 4, and more preferably from about 0.1 to about 1 ounce per hundred pounds of seed. As a soil fungicide the chemical can be incorporated in the soil or applied to the surface usually at a rate of from about 0.02 to about 20, preferably from about 0.05 to about 10, and more preferably from about 0.1 to about 5 pounds per acre. As a foliar fungicide, the toxicant is usually applied to growing plants at a rate of from about 0.01 to about 10, preferably from about 0.02 to 5, and more preferably from about 0.25 to about 1 pound per acre. pounds per acre.

Inasmuch as the pyridazinones, and the enantiomorphs, salts and complexes thereof, display fungicidal activity, these compounds can be combined with other known fungicides to provide broad spectrum activity. Suitable fungicides include but are not limited to, those compounds listed in U.S. Pat. No. 5,252,594 (see in particular columns 14 and 15).

The pyridazinones, and the enantiomorphs, acid addition salts and metal salt complexes thereof can be advantageously employed in various ways. Since these compounds possess broad spectrum fungicidal activity, they can be employed in the storage of cereal grain. These complexes can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast.

We claim:

1. A pyridazinone compound having the structure

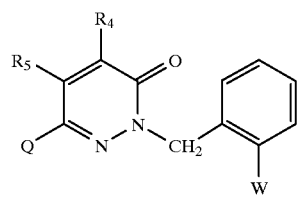

(I)

wherein W is $CH_3$—O—A=C(-)-CO(V)$CH_3$; A is N or CH; V is O or NH;

$R_4$ and $R_5$ are hydrogen;

Q is selected from a group having the following formula:

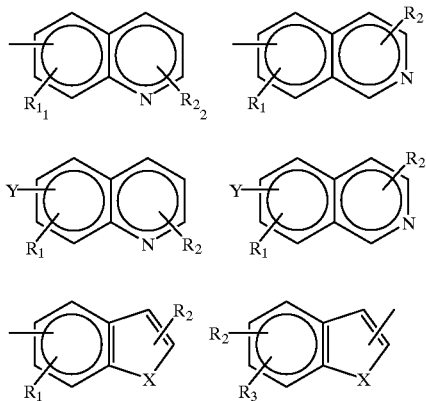

where Y is O or S and forms a direct bond to the pyridazine ring;

where $R_3$ is selected from hydrogen, halogen, cyano, nitro, trihalomethyl, methyl, phenyl, phenoxy, optionally substituted halo-substituted $(C_1-C_4)$alkyl, $(C_1-C_4)$alkylthio, $(C_1-C_4)$alkylsulfoxide and $(C_1-C_{18})$alkoxy; and $R_1$ and $R_2$ are independently selected from hydrogen, $(C_1-C_4)$alkyl, $(C_1-C_4)$alkoxy, cyano, halogen, nitro; and X is O or S.

2. The compound of claim 1 wherein A is CH.
3. The compound of claim 2 wherein V is O.
4. The compound of claim 3 wherein A is N.
5. The compound of claim 4 wherein V is O.
6. The compound of claim 4 wherein V is NH.
7. The compound of claim 3 wherein Q is bicyclic heteroaryl, halo substituted bicyclic heteroaryl, or $(C_1-C_4)$ alkylthiosubstituted bicyclic heteroaryl.
8. The compound of claim 5 wherein Q is bicyclic heteroaryl, halo substituted bicyclic heteroaryl, or $(C_1-C_4)$ alkylthiosubstituted bicyclic heteroaryl.
9. The compound of claim 6 wherein Q is bicyclic heteroaryl, halo substituted bicyclic heteroaryl, or $(C_1-C_4)$ alkylthiosubstituted bicyclic heteroaryl.
10. A fungicidal composition for controlling phytophathogenic fungi which comprises an agronomically acceptable carrier and a fungicidally effective amount of the compound of claim 1.

11. A method for controlling phytophathogenic fungi which comprises applying to the locus where control is desired a fungicidally effective amount of the compound of claim 1.

12. The method of claim 10 wherein the compound of claim 1 is applied at the rate of from about 0.05 pounds to about 50 pounds per acre.

* * * * *